United States Patent
Bauer et al.

[11] Patent Number: 6,079,562
[45] Date of Patent: *Jun. 27, 2000

[54] BAG FOR FOLDED DISPOSABLE DIAPERS

[75] Inventors: Rainer Richard Bernd Bauer, Wiesbaden; Bruce Kevin Bitowft, Glashutten; Andreas Flohr, Mulheim an der Ruhr, all of Germany

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 09/077,862
[22] PCT Filed: Nov. 27, 1996
[86] PCT No.: PCT/US96/19027
§ 371 Date: Jun. 4, 1998
§ 102(e) Date: Jun. 4, 1998
[87] PCT Pub. No.: WO97/20755
PCT Pub. Date: Jun. 12, 1997

[30] Foreign Application Priority Data

Dec. 4, 1995 [EP] European Pat. Off. .............. 95119075

[51] Int. Cl.[7] .......................... B65D 75/00; B65B 63/04; B65B 63/02; A61F 13/15
[52] U.S. Cl. ............................. 206/494; 53/429; 53/436; 53/446; 206/499; 206/526; 604/385.1
[58] Field of Search .................................. 206/494, 497, 206/499, 526; 53/143, 177, 429, 436, 446; D29/126; 604/385.1, 385.2, 358

[56] References Cited

U.S. PATENT DOCUMENTS

| | | | |
|---|---|---|---|
| 4,064,880 | 12/1977 | Logan | 604/358 |
| 4,597,494 | 7/1986 | Benoit | 706/494 X |
| 4,934,535 | 6/1990 | Muckerfuhs et al. | 706/494 |
| 5,022,216 | 6/1991 | Muckerfuhs et al. | 53/438 |
| 5,026,364 | 6/1991 | Robertson | 604/385.1 |
| 5,087,255 | 2/1992 | Sims | 604/385.1 |
| 5,346,487 | 9/1994 | Lovestedt | 604/385.1 |
| 5,361,905 | 11/1994 | McQeeny et al. | 706/494 |
| 5,722,774 | 3/1998 | Hartz | 706/494 X |
| 5,769,837 | 6/1998 | Parr | 604/385.1 X |

FOREIGN PATENT DOCUMENTS

| | | |
|---|---|---|
| 0 357 000 | 3/1990 | European Pat. Off. . |
| 0 406 928 | 1/1991 | European Pat. Off. . |
| 0 471 385 | 2/1992 | European Pat. Off. . |
| 0 618 148 | 10/1994 | European Pat. Off. . |

*Primary Examiner*—Bryon P. Gehman
*Attorney, Agent, or Firm*—Theodore P. Cummings; David M. Weirich; Steven W. Miller

[57] ABSTRACT

A bag of folded disposable diapers including folded diapers arranged in at least two superimposed stacks in a direction substantially parallel to their thickness. Each of the diapers has a pair of substantially planar surfaces which are oriented to be substantially parallel to the side panels of the bag and each diaper is folded along at least one folding line in the cross direction so as to define at least one folded area and two non-folded end areas. The diapers are arranged in the bag such that the non-folded end areas corresponding to the waist areas are positioned inwardly, away from the end panels of the flexible bag.

9 Claims, 2 Drawing Sheets

BAG FOR FOLDED DISPOSABLE DIAPERS

TECHNICAL FIELD

The present invention relates to flexible bags filled with disposable diapers, preferably compressed diapers, said articles being arranged in at least two superimposed stacks.

BACKGROUND OF THE INVENTION

Relatively soft and flexible articles such as disposable diapers, catemenial pads, incontinent briefs and the like have entered widespread use in many parts of the world over the last 20–30 years; many of these products are produced as catemenial webs which are typically folded one or more times parallel to the direction of web travel as they travel through the converting lines in the machine direction and are ultimately cut from the web to form discrete single use articles. The discrete articles are typically folded at the midpoint, collected in stacks and inserted into paperboard or cardboard cartons or flexible bags.

Flexible articles, such as disposable diapers, have been compressed prior to packing and shipping for about the last 5–7 years, to increase number of articles per bag and reduce space. Flexible bags for compressed articles are disclosed in e.g. EP A 349 050.

In one execution of such bags which is currently used in the market place two superimposed stacks of folded articles, in particularly baby diapers, are present in order to offer more articles per packaging item. Such bags have been described in e.g. EP A 406 928.

In current manufacturing/packaging methods, stacks of folded diapers in said bags are typically inserted in subsequent order, in an open flexible bag with the folded areas in each stack facing the same forward direction, and the bag being sealed at the rear of the second stack.

In the resulting package, the non-folded area of the secondly introduced stack of diapers, which correspond to the waist area of the diapers, finds itself in contact or close vicinity to the end panel formed after the sealing of the bag.

Such a configuration can lead to several disadvantages:

Indeed, the open ended area of folded diapers which typically correspond to the waist area of the articles, often contain devices like containment bands and fastening elements, which, are more collapsible compared to the rest of the diapers, and when exposed to outside pressure due to their close vicinity to the end panels, can suffer damage; indeed, especially bags filled with compressed diapers are typically quite compact and, when superimposed on to the other for transportation or storage, will have the tendency to exert pressure on any relatively weak area; such waist area of packed articles would typically constitute such a weak area;

Another issue encountered with current packing methods in the bags described above is that the sealing which occurs at the rear of the secondly introduced stack, can damage the adjacent area of the articles, which, as mentioned above, is the waist area containing collapsible features.

It has now been found that the above problems may be solved if the stacks in bags are arranged in such a way that none of the non-folded ends, corresponding to the waist area of the packed articles is in contact or in close vicinity with the end panels, but rather positioned toward the inside of the bag; It has also been found that such an arrangement provides better stability to the resulting bags, when superimposed on each other, for e.g. transportation and storage.

SUMMARY OF THE INVENTION

The present invention relates to substantially rectangular flexible bags of folded disposable diapers, preferably in a compressed state, said folded diapers being arranged in at least two superimposed stacks in a direction substantially parallel to their thickness, each of said diapers containing a crotch area designed to fit the crotch of the wearer and a waist area, designed to fit the waist of the wearer, said waist area being fitted with a containment band, each said diapers being folded along at least one folding line in the cross direction, so as to define one or more folded areas, and two non-folded end areas characterized in, that said diapers are arranged in such a way that said non-folded end areas corresponding to said waist areas fitted with a containment band are not positioned in areas capable of being directly or indirectly in contact with said end panels.

Preferably, the diapers are folded in two packs along a simple line in the mid point of the crotch area.

The present invention also relates to a method for packing diapers in flexible bags, so as to result in the configuration described herein above.

BRIEF DESCRIPTION OF THE DRAWINGS

While the specification concludes with claims particularly pointing out and distinctly claiming the present invention, it is believed the present invention will be better understood from the foregoing description in conjunction with the accompanying drawings in which:

DETAILED DESCRIPTION OF THE INVENTION

Figure 1:
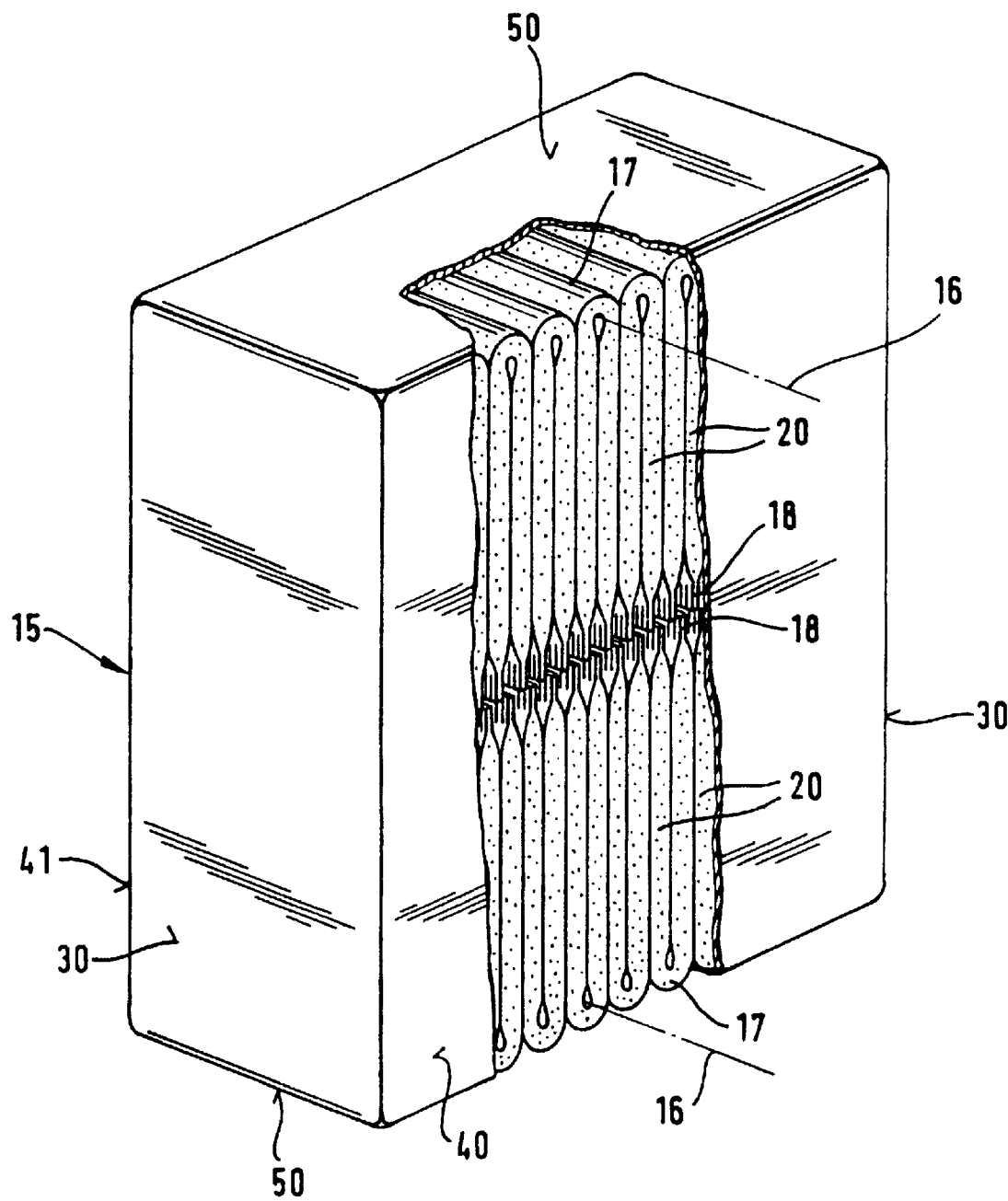
FIG. 1 is a simplified perspective view of a preferred flexible bag (15) of diapers (20) according to the present invention, in its closed configuration; showing front (40) and back (41) panels, side panels (30) and end panels (50), both end panels being folded and/or sealed; and with the diapers (20) being folded around a single folding line (16) in the cross direction, at the midpoint of their crotch area, so as to define a folded area (17) and two end areas (18).

The flexible bags of the present invention are of substantially rectangular shape and comprise a front panel and a back panel connected to one another by means of a pair of side panels, and by a pair of end panels. At least two stacks of disposable diapers, oriented so that their substantially planar surfaces are aligned substantially parallel to the side panels of the bag while the exposed peripheral edges of the articles contained within the stack are aligned substantially parallel to the front, back and end panels of the bag, are totally enclosed within the bag.

At least one of the end panels contains a sealed portion corresponding to the aperture through which the articles were introduced into the bag. At least one of the end panels may contain inwardly folded and secured side gussets; One such end panel may include an easily visible, unobstructed easy open device which may be activated by gripping between the user's fingers and pulling to create an unobstructed aperture traversing at least one corner of the bag. Alternatively, the end panels may be fitted with alternative devices designed to carry the bag such as described in e.g. EP 391460, EP 361591 and EP 439209.

The flexible bags of the present invention preferable also contain an opening device to allow to retrieve the diapers from the bag; such devices typically consists of a line of weakness having at lest a portion thereof in the side panels, and creating an opening in the side panel when the line of weakness is opened. Preferably the line of weakness is entirely positioned within one of the side panels. Such opening devices, in particular such opening devices for bags having two superimposed stacks have been described in e.g. EP A 406928.

The present invention is intended for use with disposable diapers which have a crotch area designed to fit the crotch of the wearer and a waist area, designed to fit the waist of the wearer, said waist area being fitted with a containment band;

Each said diapers is folded along at least one folding line in the cross direction, so as to define one or more folded areas, and two non-folded end areas; said diapers are arranged in such a way that said non-folded end areas corresponding to said waist areas fitted with a containment band, are not positioned in areas capable of being directly or indirectly in contact with said end panels.

The diapers are preferably baby diapers, but can also consist of diapers for incontinent adults.

The diapers herein are preferably compressed; the diapers can be compressed in the bag by at least 20% of their uncompressed thickness, and preferably by at least 30% of their uncompressed thickness. More preferably, higher levels of compression, such as 40% or, even more preferably 50–55% of the uncompressed thickness can be achieved. Levels of compression greater than 70% have been successfully achieved.

The diapers of the present invention consist of an absorbent part, designed to be placed in contact to the crotch of the wearer, said absorbent part extending in the front and the rear sides, to the waist area of the wearer, where the diapers contain a band, designed to create a separation between the absorbent part and the end of the diaper, so as to avoid wicking of fluid from the absorbent part of the diaper to the skin of the wearer. Such containment bands are typically made elastic to better fit the waist of the wearer.

Diapers fitted with waist containment band are described in e.g. EP A 202 125, EP A 376 022, EP A 627 905, EP A 396 800, EP A 494 941, WO 94/05241.

The diapers herein are folded along one folding line in the crotch area. The diapers are preferably folded in two other equal parts along one single folding line in the cross direction, said folding line being at the mid point of the crotch area. Diapers folded according to this embodiment are represented in FIG. 1.

Figure 2:
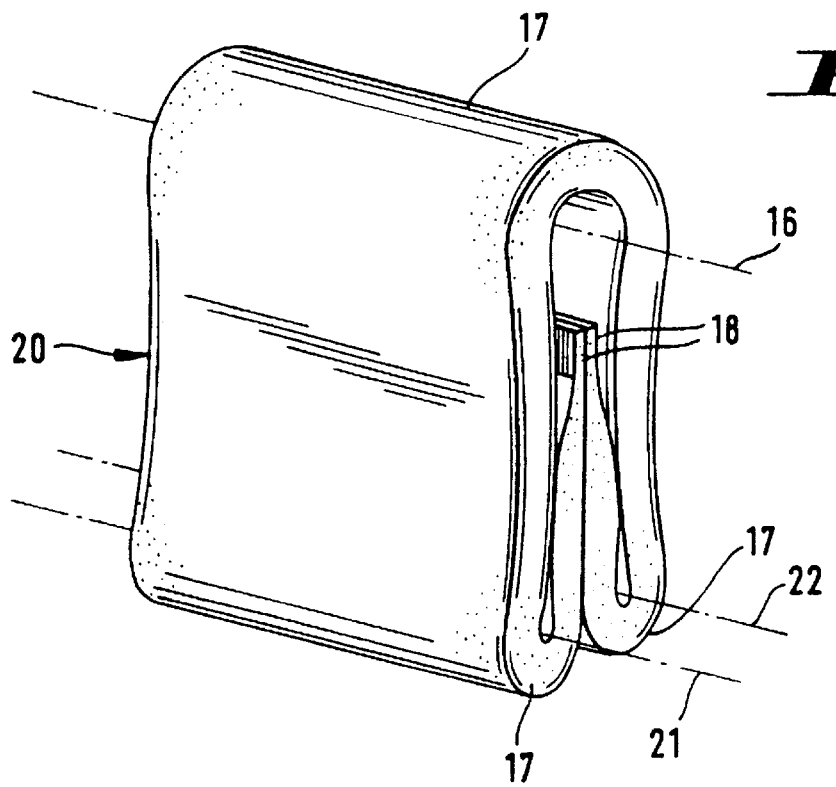
FIG. 2 represents a diaper (20 folded in four parts according to the embodiment of the invention in which two further folding lines (21, 22) are present, in addition to the main folding line (16) represented in FIG. 1, so as to create a folded area (17) and two end areas (18).

In another embodiment herein, the diapers are further folded, in four parts, along two more folding lines in the cross direction, said folding lines being between the crotch area and the end areas. A diaper folded according to this embodiment is represented in FIG. 2.

Still in another embodiment herein, the diapers are folded in three parts along two separate folding lines in the area between the crotch area and each end area.

Figure 3:
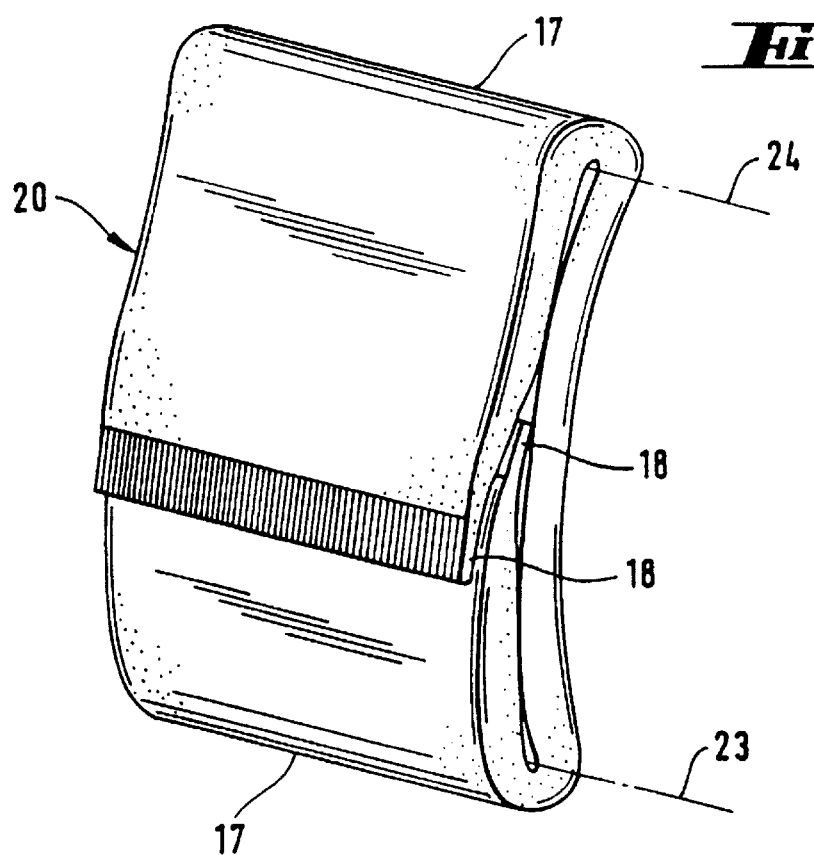
FIG. 3 represents a diaper (20) folded in three parts according to the embodiment of the invention in which two separate folding lines (23, 24), are present in the areas between the crotch and the waist areas so as to create a folded area (17) and two end areas (18)

A diaper folded according to this embodiment is represented in FIG. 3.

The bags herein contain at least two superimposed stacks of diapers; preferably the bags contain two stacks but the number of superimposed stacks can be higher, typically in the range of from 2 to 6, depending on the folding execution described above, which in turn influences the height of each stack.

The present invention also relates to a method for packing diapers.

In the method for packing disposable diapers herein, said diapers are arranged in at least two superimposed stacks of in a direction substantially parallel to their thickness, said diapers containing a crotch area designed to fit the crotch of the wearer and a waist area, designed to fit the waist of the wearer, said waist area being fitted with a containment band, said diapers being folded along at least one folding line in the cross direction, so as to define one or more folded areas, and two non-folded end areas characterized in, that said stacks are introduced in flexible bags in such a way, that said non-folded end areas corresponding to said waist area fitted with a containment band are not positioned in areas capable of being directly or indirectly in contact with the end panels of said bags.

A Preferred Method is as Follows

Prior to stacking and insertion into the bag, the diapers are typically folded one or more times in a direction generally parallel to the machine direction during converting so that the ears of each hourglass shaped diaper overlie the central portion of the diaper. The diapers are then folded according to one of the executions described herein above after being cut from a continuous web and prior to being collected into stacks. The resultant cross-section of each stack of diapers is substantially rectangular.

Prior to insertion into the bag the stacks of folded disposable diapers are preferably subjected to compression and the stacks of compressed diapers are maintained in their compressed state by the opposing side panels of the bag, which are joined to the front panel, back panel and end panels.

The stacks of diapers are then introduced successively into the preformed bag, the folded area of the first stack facing the bottom of the bag, and the folded area of the second stack facing the other end of the bag, which will be sealed to close the bag completely; the stacks are then in a mirror-like configuration, as shown in FIG. 1.

What is claimed is:

1. A substantially rectangular flexible bag of folded disposable diapers, said folded diapers being arranged in at least two superimposed stacks in a direction substantially parallel to their thickness, each said diaper having a pair of substantially planar surfaces, comprising:
   a) a flexible bag having a front and a back panel connected to one another by means of a pair of side panels and two end panels;
   b) stacks of folded, disposable diapers contained within said flexible bag, said diapers being oriented so that their substantially planar surface is aligned substantially parallel to the side panels of said bag;
   each of said diapers containing a crotch area designed to fit the crotch of the wearer and a waist area, designed to fit the waist of the wearer, each said waist area being fitted with a contaminant band;
   each said diaper being folded along at least one folding line in the cross direction, so as to define at least one folded area and two non-folded end areas such that said diapers are arranged in such a way that said non-folded end areas corresponding to said waist areas fitted with a containment band are positioned inwardly away from said end panels of said flexible bag.

2. A bag according to claim 1 wherein said diapers are compressed.

3. A bag according to claim 1 wherein said diapers are each folded along one folding line in the crotch area.

4. A bag according to claim 3 wherein said diapers are each further folded along a pair of folding lines (21–22) between said crotch area and said end areas.

5. A bag according to claim 1 wherein said diapers are folded in three parts along two separate folding lines (23–24) in the areas between the crotch area and each end areas.

6. A bag according to claim 1 wherein said diapers are baby diapers.

7. A bag according to claim 6 wherein said diapers are arranged in two superimposed stacks, and each said diaper folded along one simple folding line in the crotch area.

8. A bag according to claim 1 where said diapers are diapers for adult incontinents.

9. A method of packing disposable diapers in flexible bags wherein said diapers are arranged in at least two superimposed stacks in a direction substantially parallel to the thickness of one said diaper, said diapers containing a crotch area designed to fit the crotch of the wearer and a waist area, designed to fit the waist of the wearer, said waist area being fitted with a containment band, said diapers being folded along at least one folding line in across the width, so as to define at least one folded area, and two non-folded end areas characterized in that said stacks are introduced in said bags such that said non-folded end areas corresponding to said waist area fitted with a containment band are not positioned in areas capable of being in contact with the end panels of said bags.

* * * * *